United States Patent
Tokumaru

(10) Patent No.: US 10,023,834 B2
(45) Date of Patent: Jul. 17, 2018

(54) CULTURE APPARATUS

(71) Applicant: PANASONIC HEALTHCARE HOLDINGS CO., LTD., Tokyo (JP)

(72) Inventor: Tomoyoshi Tokumaru, Gunma (JP)

(73) Assignee: PHC Holdings Corporation, Tokyo (JP)

( * ) Notice: Subject to any disclaimer, the term of this patent is extended or adjusted under 35 U.S.C. 154(b) by 217 days.

(21) Appl. No.: 15/065,588

(22) Filed: Mar. 9, 2016

(65) Prior Publication Data

US 2016/0186122 A1 Jun. 30, 2016

Related U.S. Application Data

(63) Continuation of application No. PCT/JP2014/077158, filed on Oct. 10, 2014.

(30) Foreign Application Priority Data

Oct. 11, 2013 (JP) .................. 2013-214065

(51) Int. Cl.
*C12M 1/00* (2006.01)
*C12M 3/00* (2006.01)
(Continued)

(52) U.S. Cl.
CPC .............. *C12M 41/14* (2013.01); *B01L 1/025* (2013.01); *C12M 23/46* (2013.01); *C12M 23/48* (2013.01);
(Continued)

(58) Field of Classification Search
CPC ...... C12M 25/06; C12M 23/46; C12M 23/48; C12M 41/14; B01L 1/025; B01L 9/523; B01L 2200/141
(Continued)

(56) References Cited

U.S. PATENT DOCUMENTS 5,773,287 A 6/1998 Binder
2010/0167383 A1 7/2010 Busujima et al.
(Continued)

FOREIGN PATENT DOCUMENTS

JP 09-023877 1/1997
JP 2004-222731 A 8/2004
(Continued)

OTHER PUBLICATIONS

International Search Report issued in Application No. PCT/JP2014/077158 dated Dec. 16, 2014, with English translation.
(Continued)

*Primary Examiner* — Michael L Hobbs
(74) *Attorney, Agent, or Firm* — McDermott Will & Emery LLP

(57) ABSTRACT

A culture apparatus that cultivates a culture, which includes an outer case, an inner case configured with metal plates inside the outer case, a heater outside the inner case, and a door, which opens/closes an opening formed in front faces of the inner cases, includes: shelf rests on which side parts of a bottom plate of a shelf are to be placed, the shelf rests formed by pressing on side plates of the inner case; and a heat transfer sheet attached to an outer surface of at least one of the side plates and configured to transfer heat of the heater to the inner case, the heat transfer sheet including slits, intermittently formed, to bend the sheet to depressions of the outer surface of the side plate at positions corresponding to the shelf rests, after the heat transfer sheet is attached to the outer surface.

7 Claims, 18 Drawing Sheets

(51) Int. Cl.
    *B01L 1/02*    (2006.01)
    *C12M 1/12*    (2006.01)
(52) U.S. Cl.
    CPC ........ *C12M 25/06* (2013.01); *B01L 2200/025* (2013.01)
(58) Field of Classification Search
    USPC ...................................................... 435/303.1
    See application file for complete search history.

(56) References Cited

U.S. PATENT DOCUMENTS

| | | |
|---|---|---|
| 2012/0083030 A1 | 4/2012 | Busujima et al. |
| 2013/0078714 A1 | 3/2013 | Yamasaki et al. |

FOREIGN PATENT DOCUMENTS

| | | |
|---|---|---|
| JP | 2006-071281 A | 3/2006 |
| JP | 2010-057398 A | 3/2010 |
| JP | 2010-154792 A | 7/2010 |
| JP | 2012-075373 A | 4/2012 |

OTHER PUBLICATIONS

Chinese Office Action issued in Application No. 201480050571.4 dated Jul. 26, 2016, with English translation.

CULTURE APPARATUS

CROSS-REFERENCE TO RELATED APPLICATIONS

This is a continuation application of International Patent Application No. PCT/JP2014/077158 filed Oct. 10, 2014, which claims the benefit of priority to Japanese Patent Application No. 2013-214065 filed Oct. 11, 2013. The full contents of the International Patent Application are incorporated herein by reference.

BACKGROUND

Technical Field

The present disclosure relates to a culture apparatus.

Description of the Related Art

For example, a culture apparatus including a heater is known (for example, Japanese Patent Application Laid-Open Publication No. 2010-154792).

In a culture apparatus according to Japanese Patent Application Laid-Open Publication No. 2010-154792, a heater is arranged outside an inner case. However, in this culture apparatus, for example, it might be difficult to transfer heat of the heater to a part, of the inner case, away from the heater.

SUMMARY

A culture apparatus configured to cultivate a culture comprising: an outer case; an inner case configured with metal plates, the inner case being arranged inside the outer case; a heater arranged outside the inner case; a door configured to open and close an opening formed in front faces of the inner case; shelf rests on which side parts on both sides of a bottom plate of a shelf are to be placed, the shelf rests being formed, by press working, in side plates on both sides of the inner case; and a heat transfer sheet attached to an outer surface of at least one of the side plates of the inner case, the heat transfer sheet configured to transfer heat of the heater to the inner case, the outer surface having first depressions at locations corresponding to the shelf rests, wherein the heat transfer sheet includes a plurality of first slits configured such that a part of the heat transfer sheet is bent to the first depressions, after the heat transfer sheet is attached to the outer surface of at least one of the side plates of the inner case, the plurality of first slits being intermittently formed.

Other features of the present invention will become apparent from descriptions of the present specification and of the accompanying drawings.

BRIEF DESCRIPTION OF THE DRAWINGS

For more thorough understanding of the present invention and advantages thereof, the following description should be read in conjunction with the accompanying drawings.

DETAILED DESCRIPTION

At least the following matters will be apparent from descriptions of the present specification and the accompanying drawings.

===Culture Apparatus===

Figure 1:
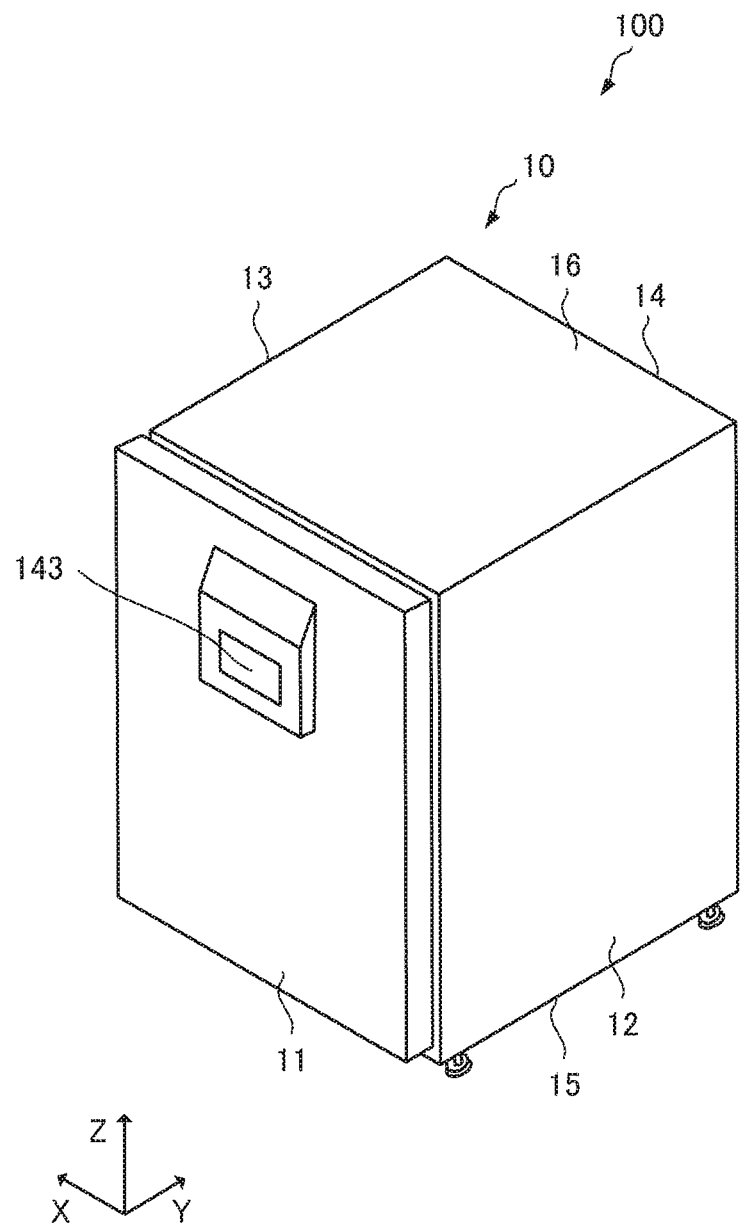
FIG. 1 is a perspective view illustrating a culture apparatus according to an embodiment.
Figure 2:
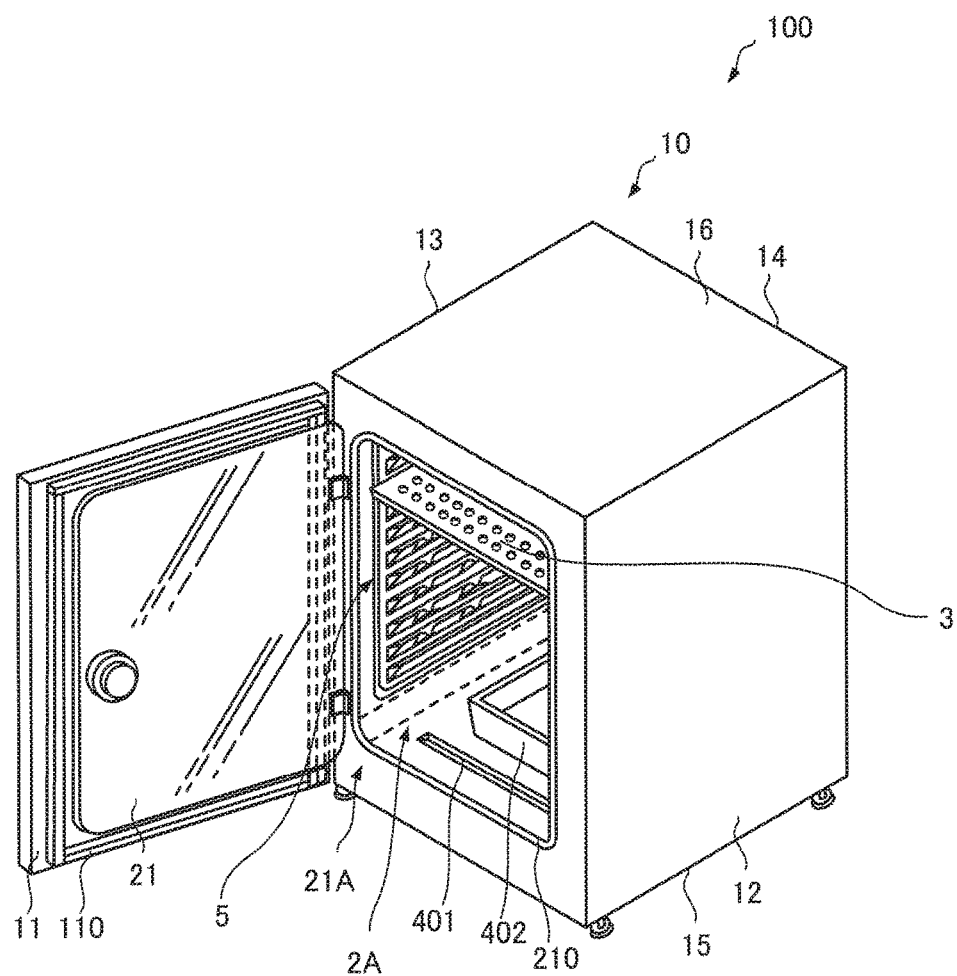
FIG. 2 is a perspective view illustrating the culture apparatus in a state where an outer door and an inner door thereof are opened according to the embodiment.
Figure 3:
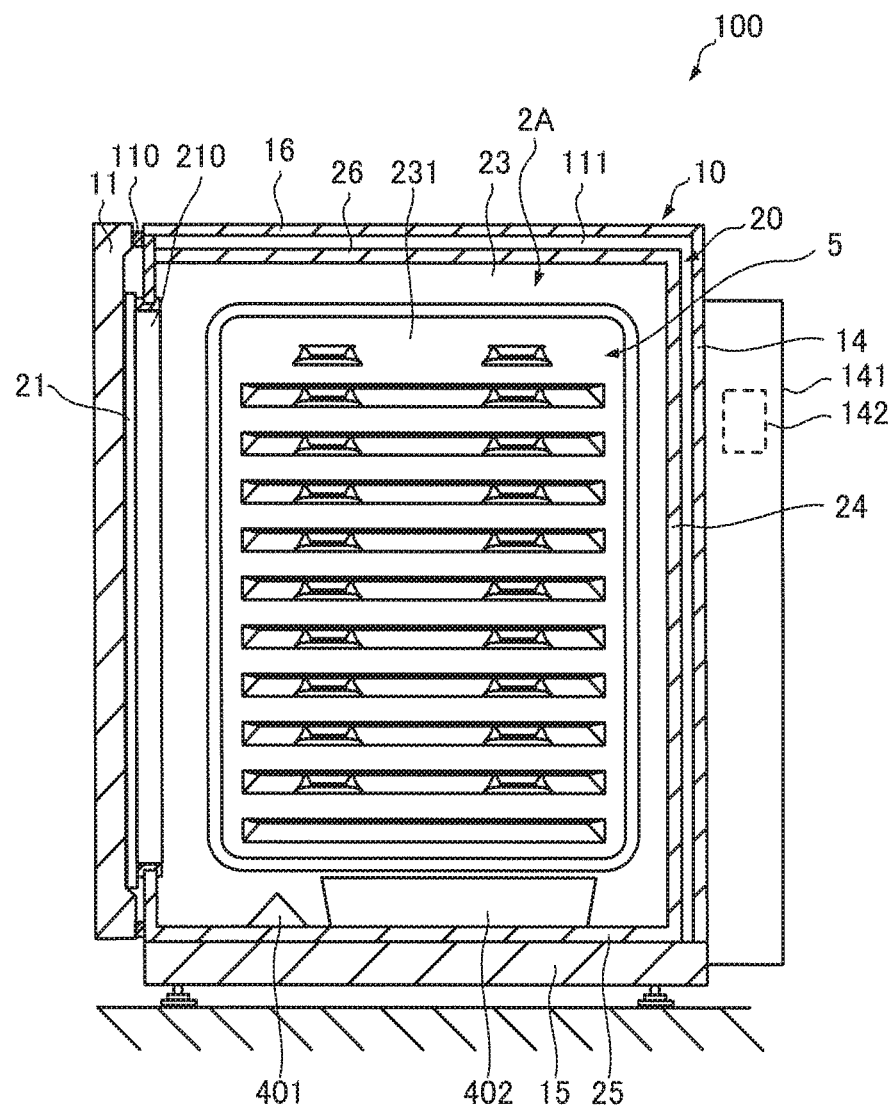
FIG. 3 is a cross-sectional view illustrating the culture apparatus according to the embodiment.
Figure 4:
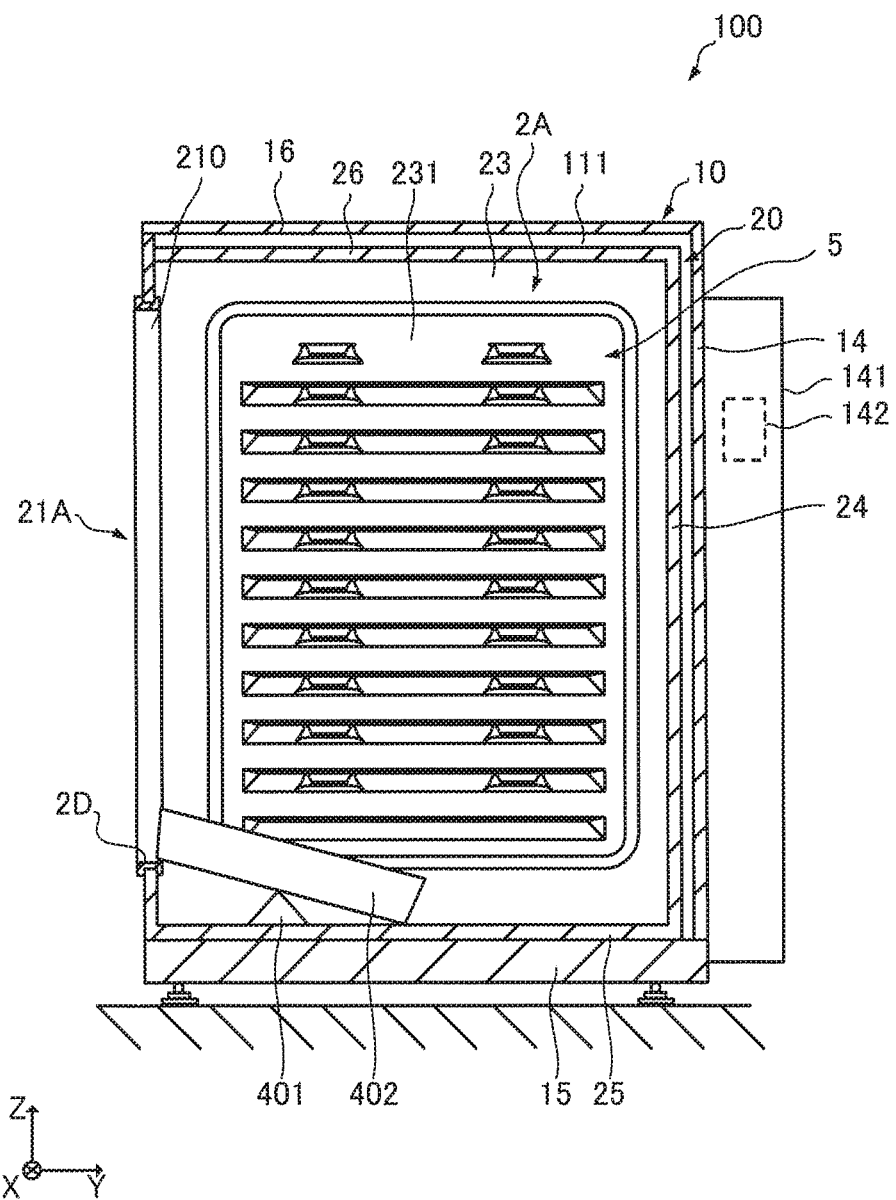
FIG. 4 is a cross-sectional view illustrating the culture apparatus in a state where the outer door thereof is omitted, according to the embodiment.

Hereinafter, a culture apparatus according to an embodiment of the present disclosure will be described with reference to FIGS. 1 to 4. FIG. 1 is a perspective view illustrating the culture apparatus according to the present embodiment. FIG. 2 is a perspective view illustrating the culture apparatus in a state where an outer door and an inner door thereof are opened according to the present embodiment. FIG. 3 is a cross-sectional view illustrating the culture apparatus according to the present embodiment. FIG. 4 is a cross-sectional view illustrating the culture apparatus in a state where the outer door is omitted according to the present embodiment. FIGS. 3 and 4 illustrate the culture apparatus 100 when viewed from a cross-section, parallel to a ZY plane, passing through substantially the center of the culture apparatus 100.

Note that an X-axis is an axis orthogonal to side plates 12, 13 of an outer case 10, and it is assumed that a direction from the side plate 12 toward the side plate 13 is a +X direction and a direction from the side plate 13 toward the side plate 12 is a −X direction. A Y-axis is an axis orthogonal to an outer door 11 and a back plate 14, and it is assumed that a direction from the outer door 11 toward the back plate 14 is a +Y direction and a direction from the back plate 14 toward the outer door 11 is a −Y direction. A Z-axis is an axis orthogonal to a bottom plate 15 and a top plate 16, and it is assumed that an up direction from the bottom plate 15 toward the top plate 16 is a +Z direction and a down direction from the top plate 16 toward the bottom plate 15 is a −Z direction.

Figure 6:
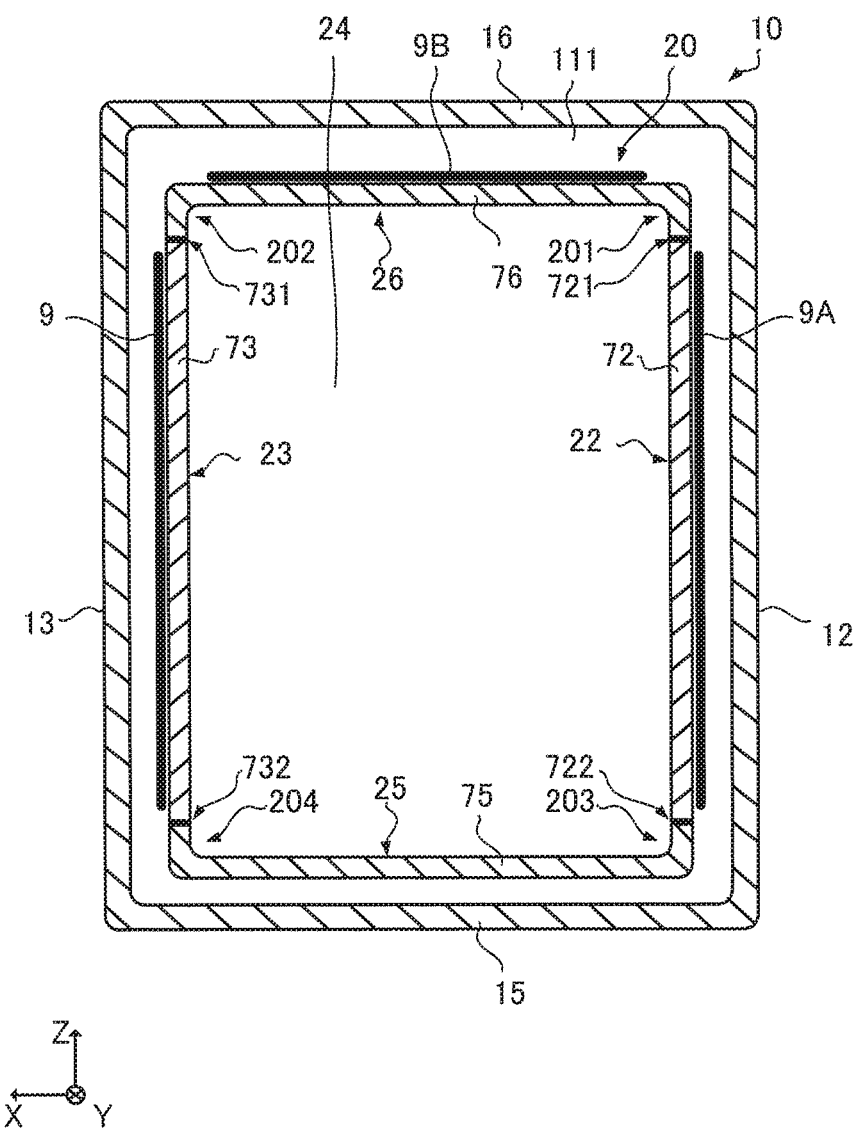
FIG. 6 is a cross-sectional view illustrating the inner case and the outer case according to the embodiment.

The culture apparatus 100 is a device configured to perform culture of a body to be cultured, such as cells, microorganisms, etc., within a culture chamber 2A. The culture apparatus 100 includes: the outer case 10; the outer door 11; an inner case 20 (FIG. 3); an inner door 21, a water tray 402, a shelf 3, a heater device 142 (FIG. 3), and heat transfer sheets 9, 9A, 9B (FIG. 6).

The outer case 10 and the inner case 20 are a substantially rectangular parallelepiped box body that is made of metal material such as stainless steel, etc. The external form of the inner case 20 is smaller than the internal form of the outer case 10 such that the inner case 20 is housed inside the outer case 10. A space 111 (FIG. 3) filled with air which exerts an effect of thermal insulation is formed between the inner case 20 and the outer case 10. Note that the space 111 may be filled with predetermined thermal insulation other than air. An opening 21A leading to the culture chamber 2A is formed in a front surface (−Y) of the outer case 10 and the inner case 20.

The outer door 11 and the inner door 21 are doors configured to open/close the opening 21A. The outer door 11 is made of a metal material, such as stainless steel, etc., is of a substantially rectangular shape greater than the outer form of the inner door 21, and is filled with thermal insulation in the interior thereof. A gasket 110 for securing airtightness inside the culture apparatus 100 is provided in the periphery of the outer door 11 on the side adjacent to the inner door 21. An operating device 143 configured to operate the culture apparatus 100 is provided to the outer door 11 on the side opposite to the inner door 21. The inner door 21 is a member made of a transparent material such as resin, glass, etc. A gasket 210 for securing airtightness inside the culture apparatus 100 is provided to a part, to be opposed to and come into contact with the inner door 21, in an edge of the opening 21A of the outer case 10.

The shelf 3 is in a substantially rectangular shape when viewed from a +Z side toward a −Z side, and is made of a metal material such as stainless steel, etc., where a body to be cultured is to be placed. Further, the shelf 3 is to be placed on the plurality of shelf rests 5, 6 provided inside the inner case 20. Note that the single shelf 3 may be provided inside the inner case 20 or the plurality of shelves 3 may be provided.

The water tray 402 is a container in which water generated when dehumidifying the culture chamber 2A is to be stored, and placed on a bottom plate 25 of the inner case 20.

Figure 14:
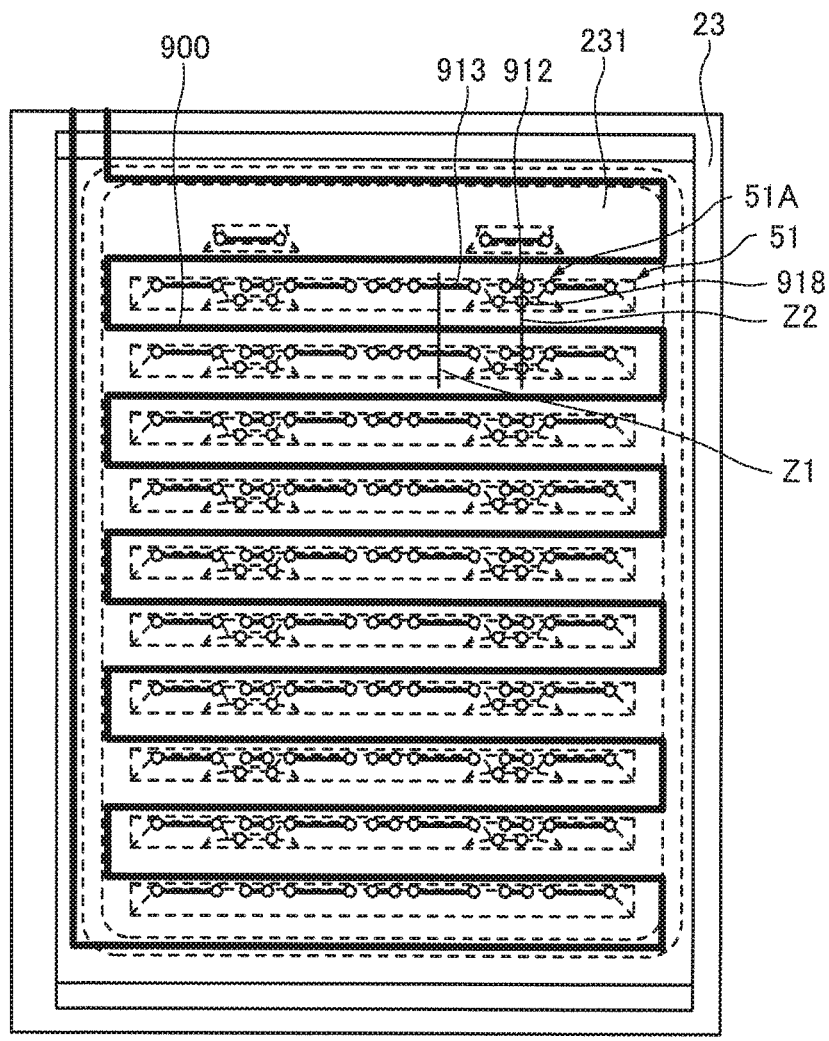
FIG. 14 is a diagram illustrating the side plate of the inner case, the heat transfer sheet, and a heater wire according to the embodiment.

The heater device 142 is a device configured to adjust temperature in the culture chamber 2A and is provided in a case 141. The heater device 142 is operated through operating the operating device 143, to dissipate heat from a heater wire 900 (FIG. 14). The heater wire 900 (heater) is attached to the heat transfer sheets 9, 9A, 9B, and the heat dissipated from the heater wire 900 is transferred to the inner case 20 and the culture chamber 2A via the transfer sheets 9, 9A, 9B (FIG. 6).

The heat transfer sheets 9, 9A, 9B are made of a material such as aluminum, etc., having relatively high thermal conductivity, and are configured to transfer the heat dissipated from the heater wire 900, etc., to the inner case 10.

===Inner Case===

Figure 5:
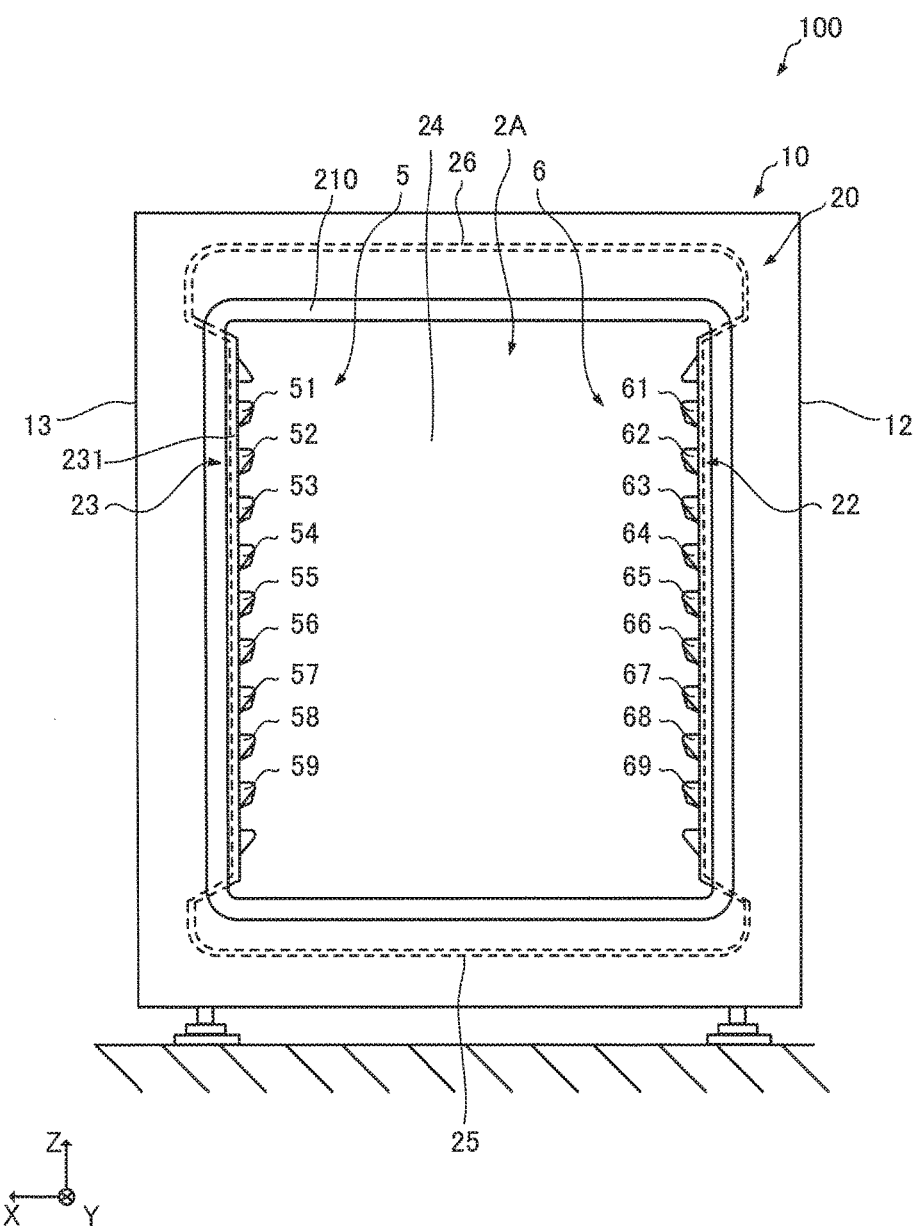
FIG. 5 is a front view illustrating the culture apparatus in a state where the outer door and the inner door are omitted according to the embodiment.

Hereinafter, the inner case according to the present embodiment will be described with reference to FIGS. 3, 5, and 6. FIG. 5 is a front view illustrating the culture apparatus in a state where the outer door and the inner door are omitted according to the present embodiment. FIG. 6 is a cross-sectional view illustrating the inner case and the outer case according to the present embodiment. Note that FIG. 6 illustrates the inner case 20 and the outer case 10 when viewed from a cross-section parallel to a ZX-plane passing through substantially the center of the culture apparatus 100 in FIG. 1 toward the +Y direction. Further, for explanation's sake, side plates 22, 23, a back plate 24, the bottom plate 25, and a top plate 26 in the inner case 20 are illustrated as plane plates, respectively.

The inner case 20 includes: the side plates 22, 23, the back plate 24, the bottom plate 25, and the top plate 26. The side plates 22, 23, the bottom plate 25, and the top plate 26 are formed by welding four metal plates 72, 73, 75, and 76. The metal plates 72, 73 are plate members that are formed into the side plates 22, 23, for example, by being pressed so that the plurality of shelf rests 5, 6 are provided in the inner case 20. The metal plate 76 is a plate member to form the top plate 26. The metal plate 76 has its ends on both sides thereof bent such that joint parts 721, 731 are positioned closer to the side plates 22, 23 than corner parts 201, 202 of the substantially rectangular parallelepiped shape of the inner case 20. The metal plate 75 is a plate member to form the bottom plate 25. The metal plate 75 has its both ends bent such that joint parts 722, 732 are positioned closer to the side plates 22, 23 than corner parts 203, 204 of the substantially rectangular parallelepiped shape of the inner case 20.

The ends on both sides of the metal plate 76 are welded to the upper ends (+Z) of the metal plates 72, 73 at the joint parts 721, 731, respectively. The ends on both sides of the metal plate 75 are welded to the lower ends (−Z) of the metal plates 72, 73 at the joint parts 722, 732, respectively. The back surface plate 24 is welded to the edges on a +Y-side of the metal plates 72, 73, 75, and 76. Accordingly, the inner case 20 is formed.

===Interior of Inner Case===

Figure 7:
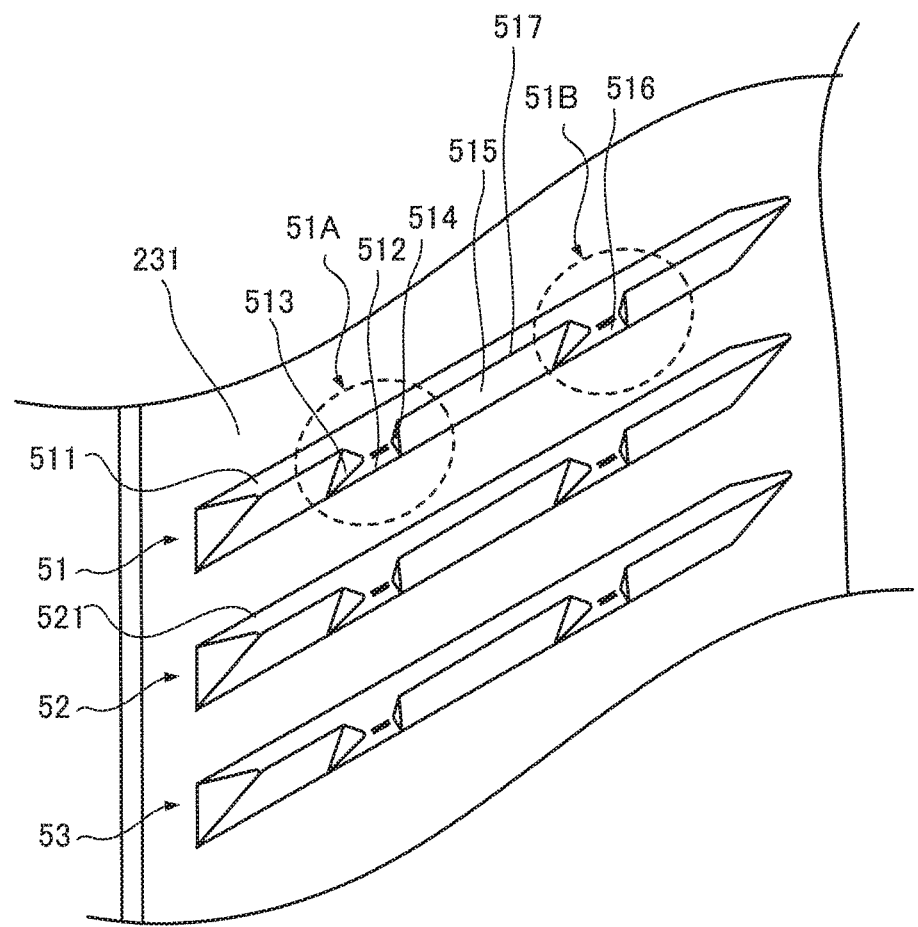
FIG. 7 is a perspective view illustrating shelf rests according to the embodiment.
Figure 8:
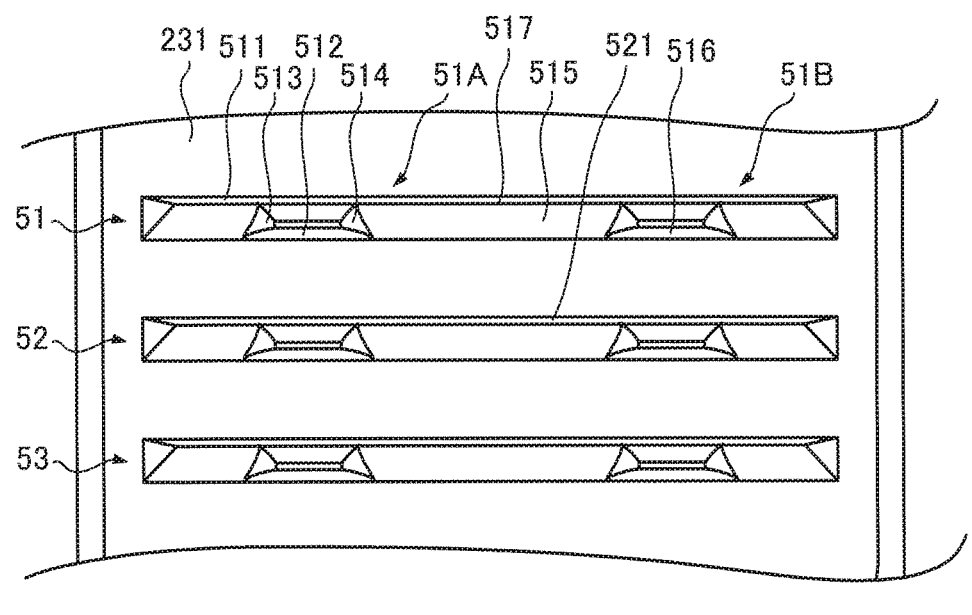
FIG. 8 is a front view illustrating the shelf rests according to the embodiment.
Figure 9:
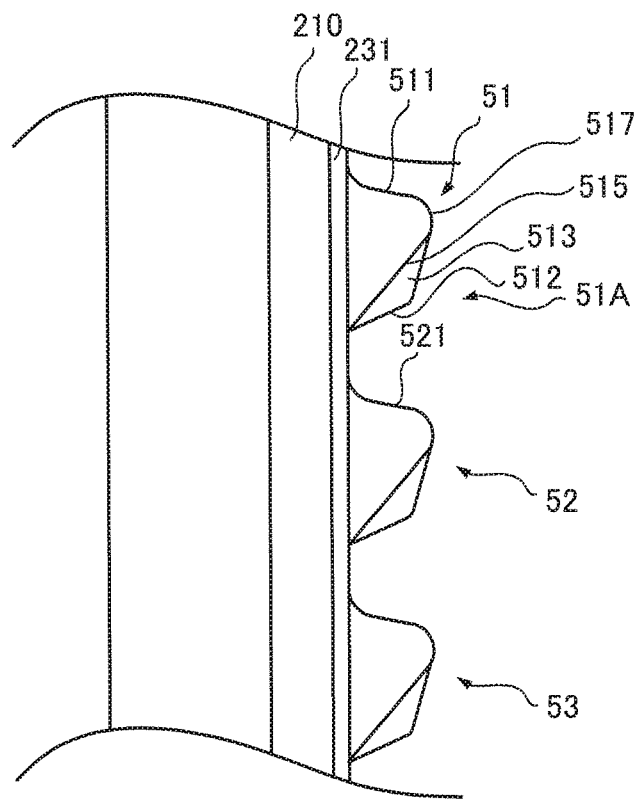
FIG. 9 is a side view illustrating the shelf rests according to the embodiment.
Figure 10:
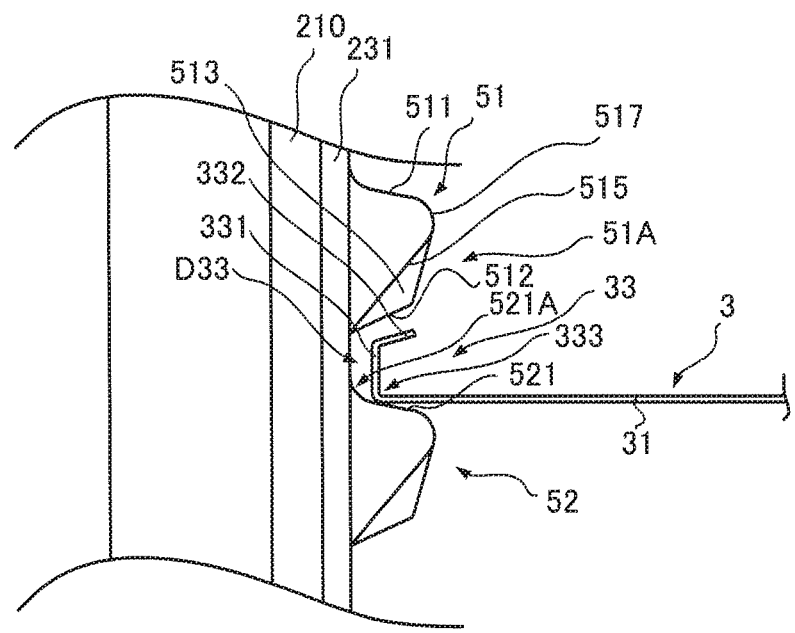
FIG. 10 is a side view illustrating the shelf rests in a state where a shelf is placed, according to the embodiment.
Figure 10:
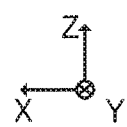

Hereinafter, the interior of the inner case according to the present embodiment will be described with reference to FIGS. 4, 5, and 6 to 10. FIG. 7 is a perspective view illustrating the shelf rests according to the present embodiment. FIG. 8 is a front view illustrating the shelf rests according to the present embodiment. FIG. 9 is a side view illustrating the shelf rests according to the present embodiment. FIG. 10 is a side view illustrating the shelf rests in a state where the shelf is placed according to the present embodiment.

The interior of the inner case 20 is in a shape symmetrical with respect to a symmetry plane which passes through the center of the inner case 20 as well as is parallel to a YZ plane. In the interior of the inner case 20, the corners thereof are chamfered so as to facilitate cleaning.

=Shelf Rest=

The shelf 3 is placed on the plurality of shelf rests 5, 6. Each respective pair of shelf rests 51 to 59 in the plurality of shelf rests 5 and shelf rests 61 to 69 in the plurality of shelf rests 6 supports the shelf 3 in a manner such that the shelf 3 will become substantially horizontal. Note that since the shelf rests 51 to 59 of the plurality of shelf rests 5 have a construction similar to that of the shelf rests 61 to 69 of the plurality of shelf rests 6, only the plurality of shelf rests 5 will be described and the description of the plurality of shelf rests 6 is omitted.

The side plate 23 is subject to press working, to form the plurality of shelf rests 5. The plurality of shelf rests 5 are provided in a rising portion 231 in the side plate 23. The rising portion 231 configure a part of the side plate 23 that has been subjected to press working so as to rise in a direction (−X) away from the side plate 13 of the outer case 10. The rising portion 231 rises closer to the center of the inner case 20 (−X) than the gasket 210 (FIG. 9) serving as the edge of the opening 21A. Accordingly, the shelf 3 placed on the plurality of shelf rests 5 is securely positioned.

The plurality of shelf rests 5 include the shelf rests 51 to 59 provided in such a manner as to be arranged in the vertical direction (Z-axis). A distance between, for example, the shelf rest 51 serving as the shelf rest on the upper side (+Z) and the shelf rest 52 serving as the shelf rest on the lower side (−Z), which are adjacent to each other in the vertical direction, is set at such a distance that movement in the vertical direction of the shelf 3 placed on the shelf rest 52 is limited to a predetermined amount. Note that the predetermined amount corresponds to, for example, a certain distance, with which the shelf 3 can be moved in the front-back (Y-axis) direction in a state of being lifted up in the vertical direction, and may be, for example, about several millimeters or several centimeters. Note that since the shelf rests 51 to 59 have similar constructions to one another, only the shelf rest 51 will be described, and the descriptions of constructions of the shelf rests 52 to 59 are omitted.

The shelf rest 51 protrudes in a direction away from the side plate 13 of the outer case 10 and has a long shape continually extending from the inner door 21 side (−Y) to the back plate 24 side (+Y). The shelf rest 51 includes a placement surface 511, an inclined surface 515, and stoppers 51A, 51B.

A side part 33 in a bottom plate 31 of the shelf 3 is placed on the placement surface 511. The placement surface 511 is inclined toward the bottom plate 25 as it goes away (−X) from the side plate 23 of the inner case 20. The placement surface 511 is formed such that the shelf 3 placed thereon is made horizontal.

The inclined surface 515 is inclined downward (−Z) as well as toward the side plate 23 from the top 517 of the shelf rest 51, such that the volume of the culture chamber 2A is increased. Note that the top 517 of the shelf rest 51 is a part of the shelf rest 51 corresponding to a position farthest from the side plate 23 in an X-axis direction. The inclined surface 515 is provided downward (−Z) from the placement surface 511. Then, the thickness between the placement surface 511 and the inclined surface 515 in the vertical direction decreases with distance from the side plate 23.

The stoppers 51A, 51B are provided in such a manner integrated into the shelf rest 51, so as to limit the movement in the vertical direction of the shelf 3 that is placed on the shelf rest 51. The stoppers 51A, 51B are provided, at positions apart from each other, along the longitudinal direction (Y-axis) of the shelf rest 51. Since the stoppers 51A, 51B have constructions similar to each other, only the stopper 51A will be described and the description of the stopper 51B is omitted.

The stopper 51A is provided, to the inclined surface 515, downward (−Z) from the placement surface 511. The stopper 51A includes a first inclined surface 512, a second inclined surface 513, and a third inclined surface 514.

The first inclined surface 512 comes into contact with the side part 33 of the shelf 3, to limit the movement of the shelf 3 in the vertical direction. The first inclined surface 512 is provided lower than the inclined surface 515 (FIG. 9). The first inclined surface 512 is inclined such that an inferior angle formed between the first inclined surface 512 and the side plate 23 becomes greater than an inferior angle formed between the inclined surface 515 and the side plate 23. The second inclined surface 513 is inclined so as to prevent the shelf 3 from being blocked by the stopper 51A when the shelf 3 is inserted into the inner case 20. The second inclined surface 513 is inclined toward the +Y direction with distance from the side plate 23. The third inclined surface 514 is inclined so as to prevent the shelf 3 from being blocked by the stopper 51A when the shelf 3 is drawn out from the inner case 20. The third inclined surface 514 is inclined toward the −Y direction with distance from the side plate 23.

=Projecting Portion=

In order to take out the water tray 402 (FIG. 4), an end portion, of the water tray 402, on the side closer (−Y) to the opening 21A is required to be lifted up in such a manner as to become higher in the vertical direction than a part 2D of the gasket 210. For example, in a case where a relatively large amount of water is stored in the water tray 402, the water in the water tray 402 may be spilled out when the end portion of the water tray 402 on a −Y side is abruptly lifted up. Note that the part 2D of the gasket 210 is apart, of the gasket 210, provided on the lower edge of the opening 21A.

A projecting portion 401 is used in taking out the water tray 402 to the outside of the inner case 20 and the outer case 10 through the opening 21A. The projecting portion 401 is formed such that the bottom plate 25 is subject to press working so as to project upward (+Z). The projecting portion 401 is provided closer to the opening 21A (−Y) in the bottom plate 25. The projecting portion 401 is in a long shape continually extending along the X-axis. The projecting portion 401 is in a chevron shape with a predetermined height. The height of the projecting portion 401 is set, at such a height that the water tray 402 can be guided, such that the end portion on the −Y side of the water tray 402 will be positioned higher than the part 2D of the gasket 210 when the water tray 402 is taken out.

When the water tray 402 is taken out, a force toward the opening 21A side (−Y) is exerted on the end portion on the −Y side of the water tray 402. With this force, the water tray 402 is moved from the +Y side toward the −Y side. The water tray 402 is guided by the projecting portion 401 such that the position in the vertical direction of the end portion on the −Y side of the water tray 402 becomes higher than the part 2D of the gasket 210, thereby being taken out to the outside of the inner case 20 and the outer case 10. Note that, at this time, the position in the vertical direction of the end portion on the −Y side of the water tray 402 becomes higher in a gradual manner with the guidance of the projecting portion 401, which prevents the water stored in the water tray 402 from being spilled out.

===Shelf===

Figure 11:
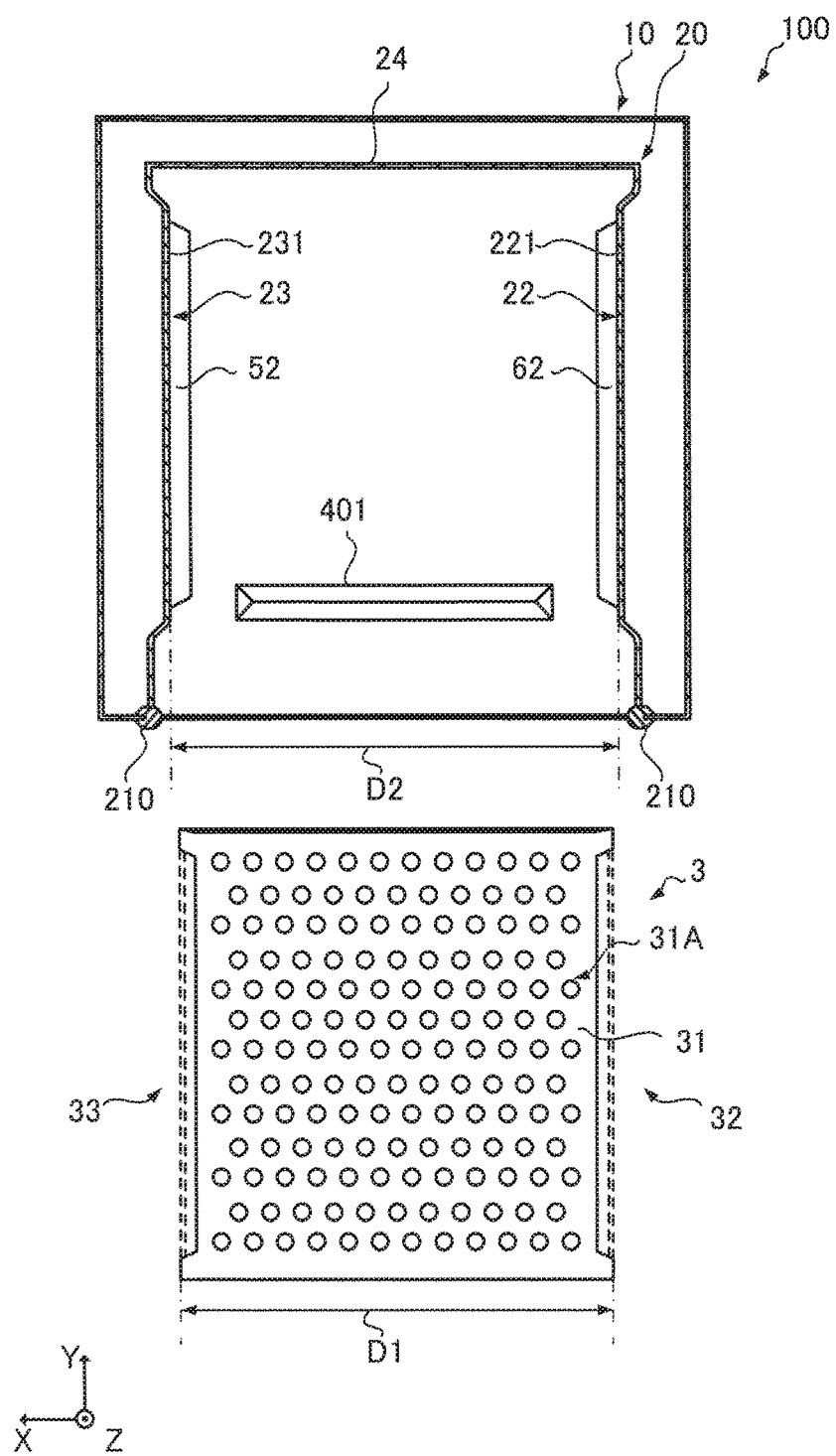
FIG. 11 is a diagram illustrating the culture apparatus and the shelf according to the embodiment.

Hereinafter, the shelf according to the present embodiment will be described with reference to FIGS. 10 and 11. FIG. 10 is a side view illustrating the shelf rest in a state where the shelf according to the present embodiment is placed thereon. FIG. 11 is a diagram illustrating the culture apparatus and the shelf according to the present embodiment. Note that FIG. 11 illustrates a plan view of the shelf. FIG. 11 further illustrates the culture apparatus 100 when viewed toward the −Z direction from a cross-section, parallel to the XY plane passing between the shelf rests 51 and 52 in the vertical direction (Z-axis) in FIG. 5.

The shelf 3 (FIG. 11) is in a shape symmetrical with respect to a symmetry plane, parallel to the YZ plane, passing through substantially the center of the shelf 3. The shelf 3 includes the bottom plate 31 and side parts 32, 33, and is integrally formed by folding a single metal plate.

The bottom plate 31 is a flat plate substantially in a rectangular shape. The bottom plate 31 includes a plurality of punched holes 31A for circulating the gas in the culture chamber 2A. A width D1 in the X-axis direction of the bottom plate 31 is set narrower than a width D2 in the X-axis direction from the rising portion 231 on the −X side to the rising portion 221 of the side plate 22. Accordingly, when the shelf 3 is placed on the shelf rest 52, a space D33 is formed between a first bent segment 331 and the rising portion 231, as well as a space similar to the space D33 is also formed between a first bent piece of the side part 32 and the rising portion 221. Since the side parts 32, 33 have constructions similar to each other, only the side part 33 will be described, and the description of the construction of the side part 32 is omitted. The side part 33 includes the first bent segment 331 (FIG. 10) and a second bent segment 332.

The first bent segment 331 is bent upward (+Z) from an end on the +X side of the bottom plate 31. The first bent segment 331 is bent such that the curvature of a bend 333 becomes greater than the curvature of a bend 521A which continues from a surface (−X) on the culture chamber 2A side in the rising portion 231 to a placement surface 521. The length in the vertical direction (Z-axis) of the first bent segment 331 is set shorter than the distance in the vertical direction from the placement surface 521 to the first inclined surface 512.

The second bent segment 332 is further bent from the first bent segment 331. The second bent segment 332 is bent from an upper end portion in the first bent segment 331 toward the center (−X) of the inner case 20. The second bent segment 332 is bent along the first inclined surface 512 of the stopper 51A and a first inclined surface 516 of the stopper 51B.

===Heat Transfer Sheet===

Figure 12:
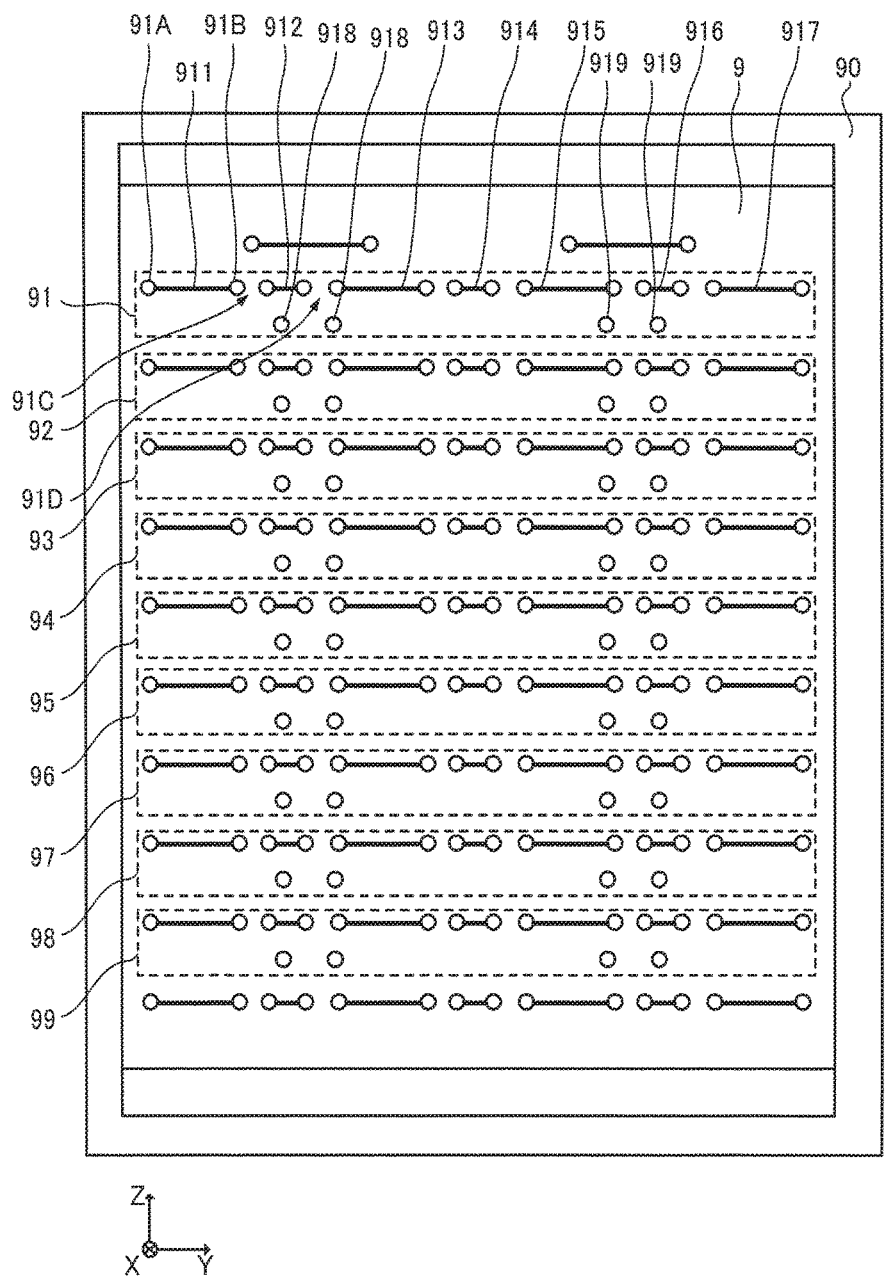
FIG. 12 is a diagram illustrating a heat transfer sheet according to the embodiment.
Figure 13:
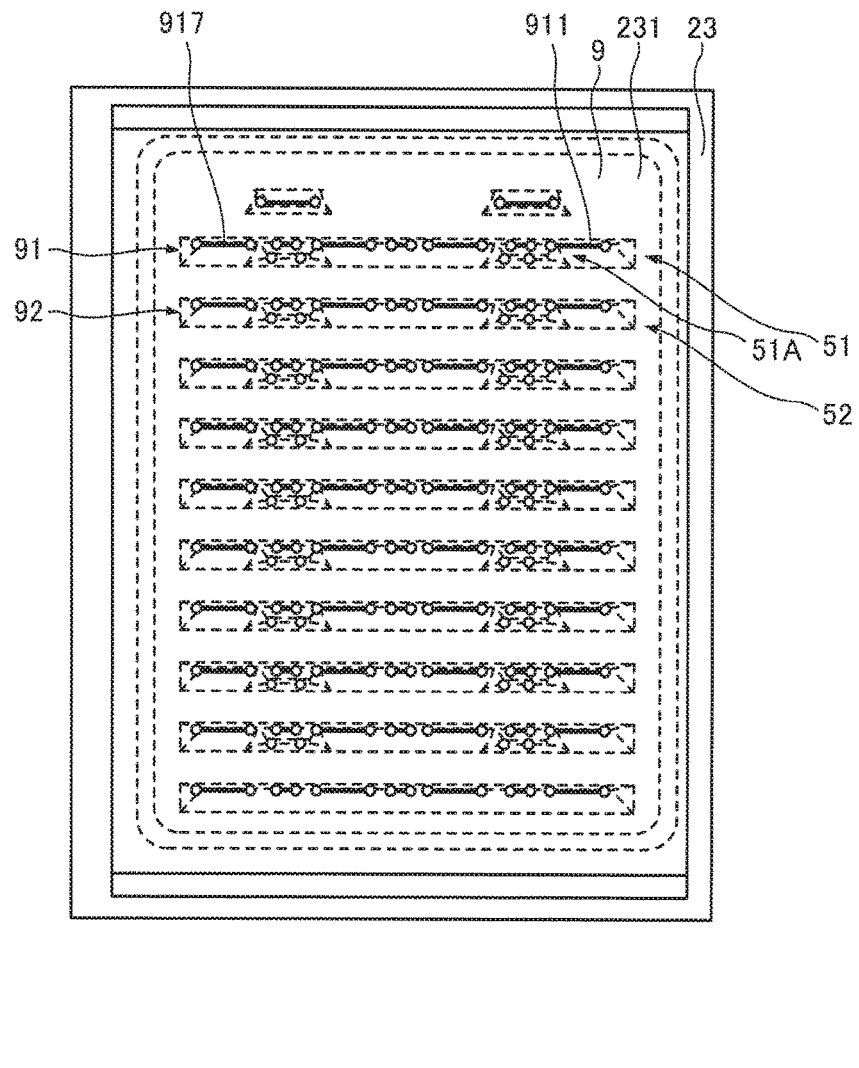
FIG. 13 is a diagram illustrating a side plate of the inner case and the heat transfer sheet according to the embodiment.
Figure 15:
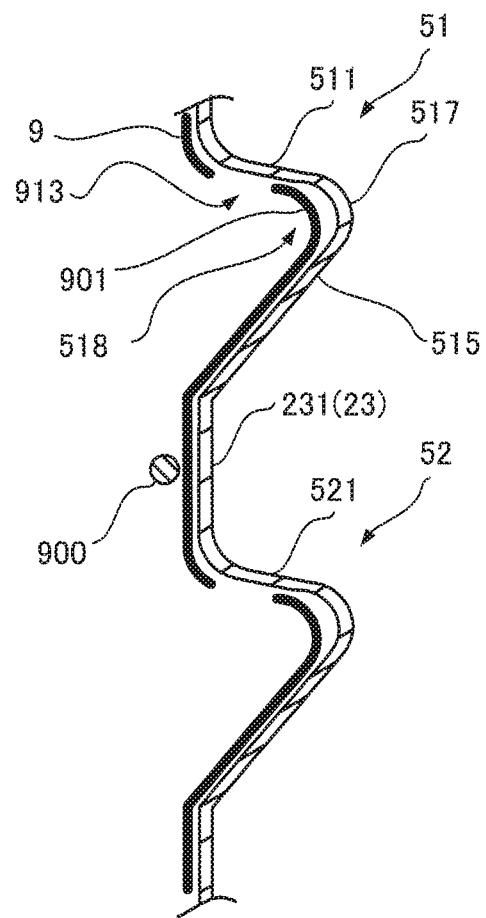
FIG. 15 is a cross-sectional view illustrating the shelf rests and the heat transfer sheet according to the embodiment.
Figure 16:
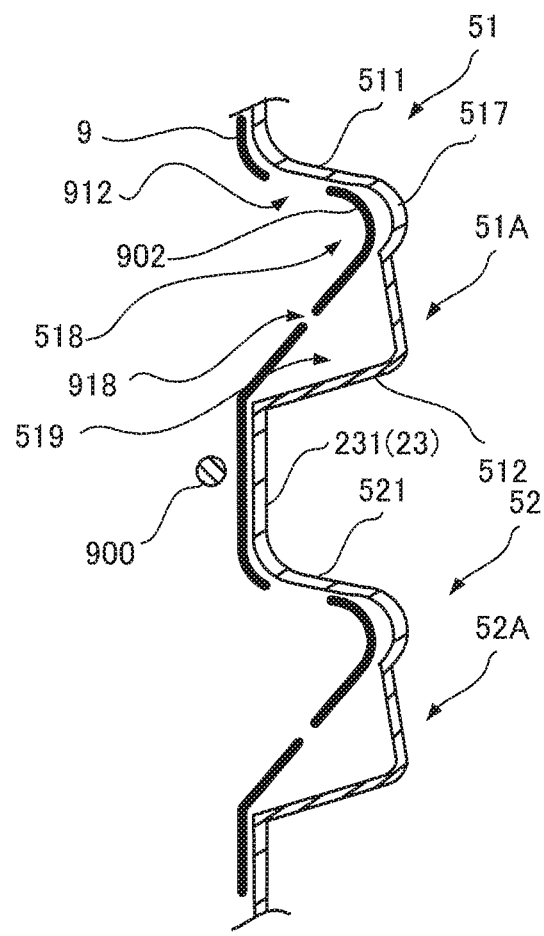
FIG. 16 is a cross-sectional view illustrating the stoppers and the heat transfer sheet according to the embodiment.
Figure 17:
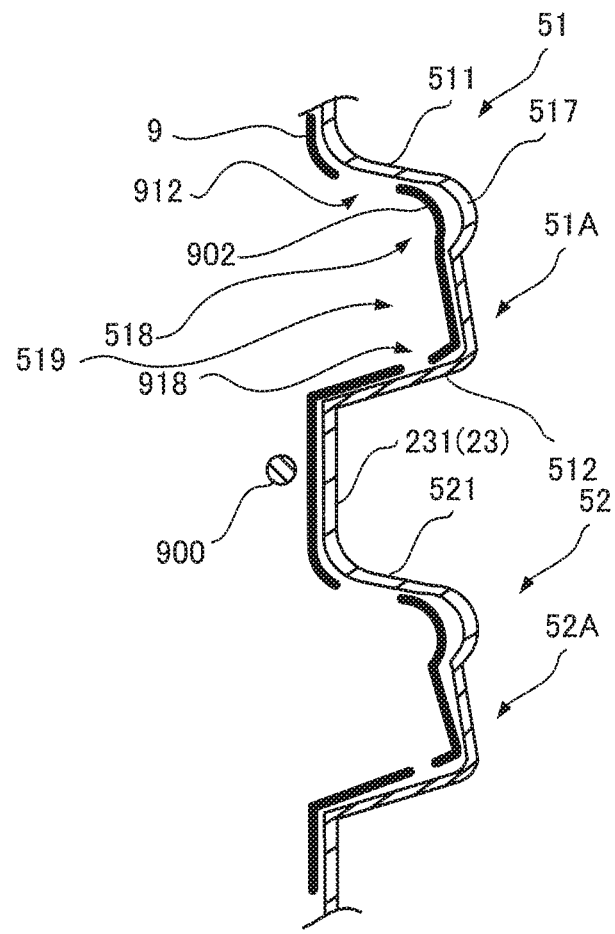
FIG. 17 is a cross-sectional view illustrating the stoppers and the heat transfer sheet in a state where the heat transfer sheet is pushed into depressions according to the embodiment.

Hereinafter, the heat transfer sheet according to the present embodiment will be described with reference to FIGS. 6 and 12 to 17. FIG. 12 is a diagram illustrating the heat transfer sheet according to the present embodiment. FIG. 13 is a diagram illustrating the side plate of the inner case and the heat transfer sheet according to the present embodiment. FIG. 14 is a diagram illustrating the side plate of the inner case, the heat transfer sheet, and the heater wire according to the present embodiment. Note that FIGS. 13 and 14 illustrate the heat transfer sheet 9 attached to a surface (+X) on the side plate 13 side (outside) of the side plate 23. FIG. 15 is a cross-sectional view illustrating the shelf rests and the heat transfer sheet according to the present embodiment. Note that FIG. 15 illustrates the side plate 23 and the like when viewed from a cross-section, including a line segment Z1 in FIG. 14 and parallel to the ZY plane, toward the +Y direction. FIG. 16 is a cross-sectional view illustrating the stoppers and the heat transfer sheet according to the present embodiment. FIG. 17 is a cross-sectional view illustrating the stoppers and the heat transfer sheet in a state where the heat transfer sheet is pushed into depressions according to the present embodiment. Note that FIGS. 16 and 17 illustrate the side plate 23 and the like when viewed from a cross-section, including a line segment Z2 in FIG. 14 and parallel to an XZ plane, toward the +Y direction. FIG. 16 illustrates the heat transfer sheet 9 not having been pushed into a depression 519. FIG. 17 illustrates the heat transfer sheet 9 having been pushed into the depression 519.

=Configuration of Heat Transfer Sheet=

The heat transfer sheets 9, 9A, 9B are configured to transfer heat dissipated from the heater wire 900 to the inner case 20. The heat transfer sheet 9 is attached to a surface (+X) on the side plate 13 side (outside) of the side plate 23. The heat transfer sheet 9A is attached to a surface (−X) of the side plate 12 side (outside) of the side plate 22. The heat transfer sheet 9B is attached to a surface (−X) of the top plate 16 side (outside) of the top plate 26. Note that since the heat transfer sheets 9, 9A have similar configurations, only the configuration of the heat transfer sheet 9 will be described and the description of that of the heat transfer 9A is omitted.

The heat transfer sheet 9 is substantially in a rectangular shape. The area of the heat transfer sheet 9 is set smaller than the area of the surface outside the side plate 23, such that the heat transfer sheet 9 can be attached to the side plate 23. Slits and release holes are provided in a first position 91 to a ninth position 99 of the heat transfer sheet 9 adjacent to each other in the Z-axis direction. The first position 91 to the ninth position 99 correspond to the locations of depressions of the outer surface of the side plate 23, formed by the press working for forming the shelf rests 51 to 59. Specifically, for example, the first position 91 corresponds to the location of the depression 518 (FIG. 15) of the side plate 23 that is depressed to form the shelf rest 51. The slits and the release holes are used to attach the heat transfer sheet 9 to the interior of the depressions of the side plate 23. Note that the slits and the release holes provided in the first position have similar configurations to those of the slits and the release holes provided in the second to ninth positions, and thus only the slits and the release holes provided in the first position 91 will be described and the descriptions of the slits and the release holes provided to the second position to the ninth position are omitted.

The plurality of slits 911 to 917 (first slit, second slit) that are formed by cutting the heat transfer sheet 9 along the Y-axis direction are intermittently provided along the Y-axis direction in the first position 91. The slits 911 to 917 are used to bent the heat transfer sheet 9 such that portions 901, 902 (FIGS. 15, 16) of the heat transfer sheet 9 are attached to the interior of the depression 518 (first depression) after the heat transfer sheet 9 is attached to the outer surface of the side plate 23. The slits 911, 913, 915, 917 have lengths similar to one another. The slits 912, 914, 916 are respectively provided between the slits 911 and 913, between the slits 913 and 915, and between the slits 915 and 917, and have lengths shorter than those of the slits 911, 913, 915, 917. Then, no slit along the Y-axis direction is provided between the slits 911 and 912, but a connection portion 91C is provided, which continues from the +Z side to −Z side of the slits 911 to 917 to connect the heat transfer sheet from the +Z side to −Z side of the slits 911 to 917. Further, a connection portion 91D having a configuration similar to that of the connection portion 91C is provided between the slits 912 and 913, and another connection portion having a configuration similar to that of the connection portion 91C is provided each between the slits in the slits 913 to 917. Thus, in the first position, three pairs of the connection portions including the connection portions 91C, 91D are to be provided along the Y-axis. With these three pairs of the connection portions, the heat transfer sheet 9 is reinforced. Further, reinforcement holes 91A, 91B for reinforcing the heat transfer sheet 9 together with the connection portions 91C, 91D are provided at both ends of slit 911.

Here, the heat transfer sheet 9 before being attached to the side plate 23 is detachably attached, using adhesive, to a pasteboard 90 for maintaining the shape of the heat transfer sheet 9. When the heat transfer sheet 9 is detached from the pasteboard 90, the heat transfer sheet 9 might be torn from the end portions of the slits, based on the force applied to the heat transfer sheet 9, without the heat transfer sheet 9 being detached from the pasteboard 90 due to an adhesive force of adhesive. However, since the heat transfer sheet 9 is reinforced with the connection portions 91C, 91D and the reinforcement holes 91A, 91B, the heat transfer sheet 9 can be reliably detached without being torn when the heat transfer sheet 9 is detached from the pasteboard 90.

Further, pairs of release holes 918, 919 are provided in the first position. The release holes 918, 919 are used to release gas generated between the heat transfer sheet 9 and the outer surface of the side plate 23 when the heat transfer sheet 9 is attached to the outer surface of the side plate 23. The release holes 918 are provided at positions facing the depression 519 (FIG. 16) of the outer surface of the side plate 23 by the press working for forming the stopper 51A. Note that the depression 519 is formed by further depressing the depression 518. The release holes 919 are also provided at positions facing a depression of the outer surface of the side plate 23 by the press working for forming the stopper 51B, similarly to the release holes 918. The release holes 918 are provided in the vicinity of the connection portions 91C, 91D, in order to improve the strength of the heat transfer sheet 9. The release holes 919 are provided in the vicinity of the connection portion between the slits 915 and 916 and the connection portion between the slits 916 and 917, similarly to the release holes 918.

=Attachment of Heat Transfer Sheet to Side Plate=

The heat transfer sheet 9 is detached from the pasteboard 90, and the surface thereof applied with adhesive is attached to the outer surface of the side plate 23 (FIG. 13).

At this time, for example, a state is such that the heat transfer sheet 9 is not attached to the inside of the depressions 518, 519 (FIGS. 15, 16).

The heat transfer sheet 9 is pressed along the depression 518 such that the parts 901, 902, etc., of the heat transfer sheet 9 are attached to the inside of the depressions 518 and 519 (second depression). At such time, the connection portions 91C, 91D, etc., are pressed to be cut, thereby connecting between the slits 911 and 912 and connecting between the slits 912 and 913, resulting in a long slit with a released end which can easily be pressed into the depression 518, etc., and accordingly the heat transfer sheet 9 is bent from the +X-side toward the −X-side to be pressed therein (FIGS. 15, 16). Further, the interior of the depression 519 is in a state where the heat transfer sheet is not attached (FIG. 16). However, since the depression 519 is a depression corresponding to the stopper 51A, having a less length, the heat transfer sheet 9 is pressed into the depression 519, thereby being able to be brought along the depression by virtue of the extension of the material such as aluminum, etc. (FIG. 17) At this time, the periphery of the depression 519 and the heat transfer sheet 9 adhere to each other with adhesive, and thus the gas generated between the heat transfer sheet 9 and the depression 519 of the side plate 23 is released through the release holes 918, etc. Therefore, the heat transfer sheet 9 is reliably attached to the outer surface of the side plate 23 having the depressions 518, 519, etc., formed therein (FIG. 14).

=Moving in and Out of Shelf=

Figure 18:
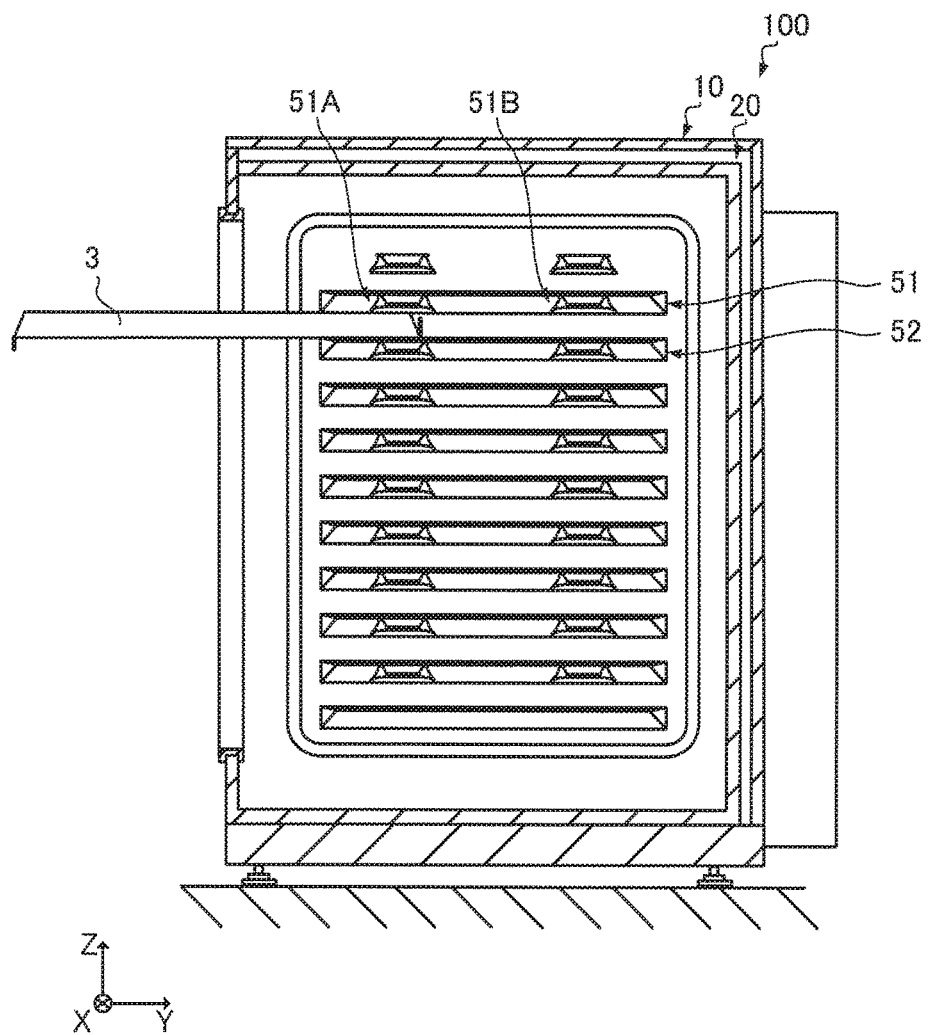
FIG. 18 is a side view illustrating the shelf and the culture apparatus according to the embodiment.

Hereinafter, moving in and out of the shelf according to the present embodiment will be described with reference to FIGS. 2, 10, and 18. FIG. 18 is a side view illustrating the shelf and the culture apparatus according to the present embodiment. Note that the side plates 22, 12 of the culture apparatus 100 are omitted for explanation's sake.

=When Inserting Shelf=

The outer door 11 and the inner door 21 are opened to bring a state where the shelf 3 can be inserted into the inner case 20 through the opening 21A.

The shelf 3 is moved from the front side (−Y) toward the back side (+Y), for example, between the shelf rests 52, 62 and the shelf rests 51, 61, in such a manner as to be placed on the shelf rests 52, 62. At this time, the movement of the side part 33 is guided by the placement surface 521 located lower (−Z) than the shelf 3 (FIG. 10) and the inclined surface 515 located above the shelf 3.

The shelf 3 is moved inside the inner case 20, to be placed on the shelf rests 52, 62. At this point, since the placement surface 521 is inclined, the side part 33 of the shelf 3 comes in line contact with the shelf rest 52. Thus, it becomes possible to fill the culture chamber 2A with sterilizing gas, to reliably sterilize the interior of the inner case 20. Note that the side part 32 also comes into line contact with the shelf rest 62, similarly to the side part 33.

Note that the curvature of the bend 333 in the side part 33 is set greater than the curvature of the bend 521A. The shelf 3 slides down the placement surface 521 in such a manner as to be positioned at the predetermined location, and thus the positioning of the shelf 3 in the X-axis direction is reliably performed.

After the shelf 3 is inserted, the inner door 21 and the outer door 11 are closed.

=When Drawing Out Shelf=

The outer door 11 and the inner door 21 are opened to bring a state where the shelf 3 in the inner case 20 can be drawn out through the opening 21A.

The shelf 3 placed on the shelf rests 52, 62 is moved from the back side toward the front side. The movement thereof in the vertical direction is limited by the stoppers 51A and 52A, and thus, for example, the shelf 3 can be prevented from being inclined to fall off during its movement. Note that the shelf 3 being inclined indicates that the front end portion of the shelf 3 is inclined in such a manner as to become lower than the back end portion. Further, the side part 33 in the shelf 3 comes into contact with the first inclined surfaces 512, 516 of the stoppers 51A, 51B provided to the upper shelf rest 51, which prevent an angle of inclination of the shelf 3 from further increasing, thereby reliably preventing the shelf 3 from falling off. Note that the second bent segment 332 of the shelf 3 is formed along the first inclined surfaces 512, 516, which prevents, for example, the side part 33 and the first inclined surfaces 512, 516 from being partially shaven to generate dust, when the second bent segment 332 comes into contact with the first inclined surfaces 512, 516.

After the shelf 3 is drawn out, the inner door 21 and the outer door 11 are closed.

As described above, the culture apparatus 100 is a device configured to cultivate a culture inside the inner case 20. The culture apparatus 100 includes the outer case 10; the inner case 20; the outer door 11; and the inner door 21. The inner case 20 is configured with the metal plates 72, 73, 75, 76, etc., and is arranged inside the outer case 10. The outer door 11 and the inner door 21 are configured to open/close the opening 21A. The culture apparatus 100 further includes the shelf rests 5, 6 and the heat transfer sheet 9. The shelf rests 5, 6 are formed, by press working, in the side plates 22, 23 of the inner case 20, and side parts 32, 33 on both sides of the bottom plate 31 (bottom surface) of a shelf 3, where the culture is to be placed, are to be placed on the shelf rests 5, 6. The heat transfer sheet 9 is attached to the outer surface of the side plate 23 of the inner case 20, and is configured to transfer heat of the heater wire 900 to the inner case 20, the outer surface having the depressions 518, 519 at locations corresponding to the shelf rest 51. The heat transfer sheet 9 includes the release holes 918, 919 and the plurality of slits 911 to 917 configured such that a part of the heat transfer sheet 9 is bent to the depressions 518, 519, after the heat transfer sheet 9 is attached to the outer surface of the side plate 23 of the inner case 20, the release holes 918, 919 and the plurality of slits 911 to 917 being intermittently formed. Thus, the heat of the heater wire 900 can be reliably transferred, via the heat transfer sheet 9, to the position apart from the heater wire 900 in the side plate 23 of the inner case 20. Further, supports, etc., for supporting the shelf 3 are not provided inside the inner case 20, which facilitates cleaning of the interior of the inner case 20. Further, supports, etc., for supporting the shelf 3 are not required to be provided inside the inner case 20, which enables reduction in the number of components of the culture apparatus 100, thereby enabling reduction in the manufacturing costs of the culture apparatus 100.

Further, the heat transfer sheet 9 includes release holes 918 configured to allow gas to be released, the gas being generated when the heat transfer sheet 9 is attached to the surface having the depressions 518, 519 of the side plate 23 of the inner case 20. With the gas being released, the heat transfer sheet 9 can be brought along the depression 519. This increases the area of the heat transfer sheet 9 having contact with the side plate 23, thereby being able to reliably transfer the heat of the heater wire 900 to the inner case 20.

Further, the shelf rest 51 is in a long shape. The slits 911 to 917 are formed by cutting the heat transfer sheet 9 along the longitudinal direction (Y-axis) of the shelf rest 51. Such configurations facilitate work of attaching the heat transfer sheet 9 to the depression 518. Thus, the culture apparatus 100, which is excellent in mass productivity and is capable of being relatively easily manufactured, can be provided.

Further, the side plate 23 of the inner case 20 further includes a stopper 51A formed by press working such that the stopper 51A protrudes toward inside the inner box, the stopper 51A being configured to limit the movement in the vertical direction of the shelf 3 placed on the shelf rest 52. The release holes 918 are provided at positions facing the depression 519 that is formed in the depression 518 at locations corresponding to the stopper 51A. The heat transfer sheet 9 is bent in such a manner as to be attached to the depression 519 as well as the depression 518. Thus, with the stopper 51A being further formed in the shelf rest 51, the release holes 918 are to be provided at positions facing the depression 519, so as to discharge the gas in the space surrounded by the adhesive of the heat transfer sheet 9 around the stopper 51A. Accordingly, the reliable release of the gas generated when the heat transfer sheet 9 is attached to the side plate 23 of the inner case 20 enables reliable transfer of the heat of the heater wire 900 to the inner case 20.

Note that a present embodiment is simply for facilitating the understanding of the present disclosure, and is not in any way to be construed as limiting the present disclosure. The present disclosure may variously be changed or altered without departing from its spirit and encompass equivalents thereof It has been described, in the above embodiment, that the heater wire 900 is provided between the outer case 10 and the inner case 20, to dissipate heat from the heater wire 900, but it is not limited thereto. For example, a cooling apparatus including an evaporator configured to absorb heat may be provided between the outer case 10 and the inner case 20. And the heat of the culture chamber 2A may be absorbed by the cooling apparatus through the inner case 20 and the heat transfer sheet 9. Further, for example, both the heater wire 900 and the evaporator may be provided between the outer case 10 and the inner case 20, to dissipate heat from the heater wire 900 and/or absorb heat with the evaporator.

Further, it has been described, in the above embodiment, that the heat transfer sheets 9, 9A, 9B are attached to the inner case 20, but it is not limited thereto. For example, another heat transfer sheet may be attached to a surface (−Z) on the bottom plate 15 side of the bottom plate 25. Furthermore, for example, only at least one of the heat transfer sheets 9, 9A may be attached.

Further, it has been described, in the above embodiment, that a surface of the heat transfer sheet 9 applied with adhesive shows up when the heat transfer sheet 9 is peeled off from the pasteboard 90, and is attached to the side plate 23, but it is not limited thereto. For example, the adhesive may be applied to an outer surface 51A, 51B may be provided extending from the inclined surface of the side plate 23, and also the adhesive may be applied to both of the heat transfer sheet 9 and side plate 23.

Further, it has been described, in the above embodiment, that the release holes 918 are provided at positions facing the depression 519, but it is not limited thereto. For example, the release holes 918 may be provided at positions facing the depression 518, and also may be provided at positions facing the side plate 23.

Further, it has been described, in the above embodiment, that two stoppers 51A, 51B are provided to the shelf rest 51 in the longitudinal direction (Y-axis) thereof, but it is not limited thereto. For example, one single stopper having a configuration similar to that of the stopper 51A may be provided to the shelf rest 51 in the longitudinal direction, and also three or more stoppers may be provided. Furthermore, for example, one single stopper may be in a long shape along the longitudinal direction (Y-axis) of the shelf rest 51.

Further, it has been described, in the above embodiment, that the stoppers 51A, 51B are provided to the inclined surface 515, but it is not limited thereto. For example, the stoppers 51A, 51B may be provided extending from the inclined surface 515 to the rising portion 231 of the side plate 23 below (−Z of FIG. 7) the inclined surface 515.

Further, it has been described, in the above embodiment, that the inner case 20 is formed such that the joint parts 721, 731 are located closer to the side plates 22, 23 with respect to the corner parts 201, 202 of the inner case 20, and the joint parts 722, 732 are located closer to the side plates 22, 23 with respect to the corner parts 203, 204 of the inner case 20, but it is not limited thereto. For example, the inner case 20 may be formed such that the joint parts 721, 731 are located closer to the top plate 26 with respect to the corner parts 201, 202, and the joint parts 722, 732 are located closer to the bottom plate 25.

Further, it has been described, in the above embodiment, that the first bent segment 331 is bent such that the curvature of the bend 333 (FIG. 10) will be greater than the curvature of the bend 521A, but it is not limited thereto. For example, the first bent segment 331 may be bent such that the curvature of the bend 333 will be less than the curvature of the bend 521A. In this case, a space is formed between the side part 33 of the shelf 3 placed on the placement surface 521 and, the rising portion 231 and placement surface 521. This enables sterilizing gas in the culture chamber 2A to be introduced into this space, thereby being able to reliably sterilize the inside of the culture chamber 2A.

Further, it has been described, in the above embodiment, that the projecting portion 401 (FIG. 4) is in a long shape continued along the X-axis, but it is not limited thereto. For example, a plurality of projections having a function similar to that of the projecting portion 401 may be provided along the X-axis, and also a single projection in the plurality of projections may be provided.

Further, in the above embodiment, it has been described that a single metal plate is folded to integrally form the shelf 3, but it is not limited thereto. For example, the side parts 32, 33 may be welded to the bottom plate 31, to form the shelf 3.

What is claimed is:

1. A culture apparatus configured to cultivate a culture comprising:
    an outer case;
    an inner case configured with metal plates, the inner case being arranged inside the outer case;
    a heater arranged outside the inner case;
    a door configured to open and close an opening formed in a front face of the inner case;
    shelf rests on which side parts on both sides of a bottom plate of a shelf are to be placed, the shelf rests being formed, by press working, in side plates on both sides of the inner case; and
    a heat transfer sheet attached to an outer surface of at least one of the side plates of the inner case, the heat transfer sheet configured to transfer heat of the heater to the inner case, the outer surface having first depressions at locations corresponding to the shelf rests,
    wherein the heat transfer sheet includes a plurality of first slits configured such that a part of the heat transfer sheet is bent to the first depressions, after the heat transfer sheet is attached to the outer surface of at least one of the side plates of the inner case, the plurality of first slits being intermittently formed.

2. The culture apparatus according to claim 1, wherein the heat transfer sheet includes release holes configured to allow gas to be released, the gas being generated when the heat transfer sheet is attached to the outer surface of at least one of the side plates of the inner case.

3. The culture apparatus according to claim 2, wherein the shelf rests are in a long shape, and
    the first slits are formed by cutting the heat transfer sheet along a longitudinal direction of the shelf rests.

4. The culture apparatus according to claim 2, wherein the shelf rests are in a long shape, and
    the first slits are formed by cutting the heat transfer sheet along a longitudinal direction of the shelf rests.

5. The culture apparatus according to claim 2, wherein:
    the at least one of the side plates of the inner case further includes stoppers formed by press working such that the stoppers protrude toward inside the inner box, the stoppers being configured to limit movement in a vertical direction of a shelf placed on immediately lower shelf rests,
    the release holes are provided at positions facing second depressions, the second depressions being formed in the first depressions at locations corresponding to the stoppers, and
    the heat transfer sheet further includes second slits configured such that a part of the heat transfer sheet is bent to the second depressions, after the heat transfer sheet is attached to the outer surface of the at least one of the side plates of the inner case.

6. The culture apparatus according to claim 3, wherein the side plates of the inner case each have further formed therein stoppers by further depressing the first depressions by press working, the stoppers being configured to limit movement in a vertical direction of the shelf placed on the shelf rests,
    the release holes are provided at positions facing second depressions, the second depressions being formed in the first depressions with the stoppers being formed, and
    the heat transfer sheet further includes second slits to bend the heat transfer sheet in such a manner as to be further attached to the second depressions, after being attached to the outer surface of the side plate of the inner case.

7. The culture apparatus according to claim 4, wherein the side plates of the inner case each have further formed therein stoppers by further depressing the first depressions by press working, the stoppers being configured to limit movement in a vertical direction of the shelf placed on the shelf rests,
    the release holes are provided at positions facing second depressions, the second depressions being formed in the first depressions with the stoppers being formed, and
    the heat transfer sheet further includes second slits to bend the heat transfer sheet in such a manner as to be further attached to the second depressions, after being attached to the outer surface of the side plate of the inner case.

* * * * *